United States Patent [19]

Werner et al.

[11] Patent Number: 4,495,369

[45] Date of Patent: Jan. 22, 1985

[54] PROCESS FOR THE PREPARATION OF NEOPENTYLAMINE

[75] Inventors: Friedrich Werner, Cologne; Heinz U. Blank, Odenthal; Günther Gramm, Cologne; Rudolf Braden, Odenthal; Heinz Ziemann, Leichlingen, all of Fed. Rep. of Germany

[73] Assignee: Bayer Aktiengesellschaft, Leverkusen, Fed. Rep. of Germany

[21] Appl. No.: 304,532

[22] Filed: Sep. 22, 1981

Related U.S. Application Data

[63] Continuation of Ser. No. 166,269, Jul. 2, 1980, abandoned.

[30] Foreign Application Priority Data

Jul. 17, 1979 [DE] Fed. Rep. of Germany ....... 2928742

[51] Int. Cl.$^3$ .............................................. C07C 85/06
[52] U.S. Cl. ..................................... 564/480; 564/479
[58] Field of Search .................... 564/479, 480

[56] References Cited

U.S. PATENT DOCUMENTS 4,078,003  3/1978  Feichtinger et al. ............... 564/480

Primary Examiner—Paul F. Shaver
Attorney, Agent, or Firm—Sprung Horn Kramer & Woods

[57] ABSTRACT

A process for the preparation of neopentylamine which is virtually free from amines with a higher degree of alkylation which comprises contacting neopentanol with ammonia at a temperature of 200° to 300° C. in the presence of a hydrogenation catalyst. The process can be carried out under increased pressure and in the presence of catalytic amounts of hydrogen.

11 Claims, No Drawings

PROCESS FOR THE PREPARATION OF NEOPENTYLAMINE

This is a continuation of application Ser. No. 166,269, filed July 2, 1980, now abandoned.

The invention relates to a process for the preparation of neopentylamine.

Neopentylamine is known and has been obtained, for example, by hydrogenation of trimethylacetaldoxime on Raney nickel (J. Am. Chem. Soc. 60, 657/1938), by reduction of pivalonitrile with lithium alanate in ether (J. Am. Chem. Soc. 74, 4052 (1952)), by Hofmann degradation of tert-butylacetamide (J. Am. Chem. Soc. 71, 2808 (1949)), or by reduction of trimethylacetamide with lithium aluminum hydride (J. Am. Chem. Soc. 81, 3728 (1959)) or with diborane (J. Am. Chem. Soc. 86, 3566 (1964)). It is inappropriate to carry out these syntheses on an industrial scale, since they utilize starting substances which are themselves accessible only with difficulty and in poor yields.

It is furthermore known to react aliphatic alcohols, such as, for example, ethanol or butanol, with an approximately 6-fold molar excess of ammonia in the presence of about 6 to 9 mols of hydrogen per mol of alcohol, on nickel pellets in the gas phase to give a mixture of the corresponding mono-, di- and tri-alkylamines, yields of 25%, 45% and 10 to 15% of the theoretical yield being achieved for the 3 amines alkylated to different degrees (U.S. Pat. No. 2,365,721). Another process for the amination of aliphatic alcohols is carried out in the gas phase on a skeleton copper catalyst, which is pre-treated with barium hydroxide before the reaction, and, for example, in the reaction of ethanol with 0.9 mol of ammonia and 4.5 mols of hydrogen, in each case per mol of ethanol, a reaction mixture which contains 13% of monoethylamine, 35% of diethylamine and 19% of triethylamine is obtained.

A process has now been found for the preparation of neopentylamine of the formula: $(CH_3)_3C-CH_2-NH_2$ which is virtually free from amines with a higher degree of alkylation, characterized in that neopentanol is reacted with ammonia at a temperature of 200° to 300° C. in the presence of a hydrogenation catalyst. The process can be carried out under increased pressure and, if appropriate, in the presence of catalytic amounts of hydrogen.

Neopentanol is known and can be prepared, for example, by reacting hydrogen peroxide with diisobutylene in the presence of sulphuric acid (J. Am. Chem. Soc. 77, 3139 (1955)).

Ammonia can be employed in the process according to the invention in the form of a solution, for example an aqueous solution, or as free ammonia, such as gaseous or liquid ammonia. Liquid ammonia is preferably employed. The ammonia can be employed in the process according to the invention in an amount of, for example, 0.5 to 10 mols, preferably 1 to 5 mols, per mol of neopentanol. The unreacted ammonia can be recovered from the reaction according to the invention. It is of course possible to employ even greater amounts of ammonia than these indicated, but this is disadvantageous for economic reasons.

The process according to the invention is carried out, for example, at a temperature of 200° to 300° C., preferably of 220° to 280° C. The other process parameters, such as activity of the hydrogenation catalyst, desired conversion or given residence time, can be taken into consideration in choosing the reaction temperature within the range indicated. Thus, for example, if a relatively low conversion is desired, the catalyst has a relatively high activity and/or the given residence time is relatively long, the process can be carried out at a lower temperature within the range indicated. Conversely, a higher temperature makes either a higher conversion and/or a shorter residence time and/or the use of a hydrogenation catalyst which is less active possible. For example, a reaction temperature of 230° C. has found to be suitable for a conversion of about 50% on Raney nickel pills with a residence time of 10 minutes.

It is not critical for the success of the process according to the invention to maintain a certain pressure, and the reaction can thus be carried out under reduced pressure, under normal pressure or under increased pressure. The preferred procedure for the process according to the invention is to apply increased pressure. Increased pressure can be, for example, a pressure of 10 to 500 bars, preferably 20 to 300 bars.

The process according to the invention can be carried out either in the gas phase or in the liquid phase. The preferred procedure is that in the liquid phase. The procedure in the liquid phase under increased pressure is particularly preferred.

The process according to the invention can be carried out either discontinuously or continuously. The continuous procedure is preferred.

The process according to the invention is carried out in the presence of a catalyst which can be employed for catalyzing hydrogenation reactions or dehydrogenation reactions and hereinafter is called a hydrogenation catalyst. Hydrogenation catalysts which may be mentioned are, for example, those which contain at least one metal of group VIII of the periodic system (Mendeleev) and/or copper or at least one metal from the group comprising vanadium, chromium and manganese, in metallic and/or oxidic form. The hydrogenation catalyst can be used together with an inert support or without a support. Examples of inert supports are synthetic and naturally occurring, optionally physically or chemically modified substances, such as aluminum oxides, silicic acid, kieselguhr, silicates, aluminosilicates, montmorillonite, zeolites, spinels, kaolin, clay, magnesium silicate, asbestos, pumice, dolomite, alkaline earth metal carbonates, alkaline earth metal sulphates, zinc oxide, zirconium oxide, silicon carbide, boron phosphate, aluminum phosphate or active charcoal. Such supported catalysts in general contain about 1 to 70, preferably 5 to 65, % by weight of the catalytically active metal, relative to the total weight of supported catalyst. The catalytically active metals can be homogeneously distributed in the support or can be located in the outer layer or on the surface of the support.

The catalysts can furthermore contain one or more accelerators or activators, such as lithium, sodium, potassium, calcium, barium, silver, gold, beryllium, lanthanum, cerium, vanadium, niobium, tantalum, molybdenum or tungsten, in amounts of up to 10% by weight, preferably in amounts of up to 1% by weight.

Examples which may be mentioned of active substances, in metallic or oxidic form, for the hydrogenation catalysts which can be employed according to the invention are: palladium, platinum, ruthenium, rhodium, nickel, cobalt, iron and copper. The metals mentioned can be present in the hydrogenation catalyst according to the invention either individually or in the form of mixtures of more than one of these metals. They can furthermore be combined with a metal from the group comprising aluminum, vanadium, chromium and manganese. Preferred hydrogenation catalysts for the process according to the invention are those which contain nickel, in metallic or oxidic form, by itself or in combination with at least one of the metals mentioned, for example catalysts of the Raney type, such as Raney nickel, Raney nickel/iron, Raney nickel/cobalt, Raney nickel/copper, metallic nickel prepared by reducing nickel salts with zinc dust, alkali metal hydride, boranates, hydrogen boride, metal-alkyl compounds or hydrazine, such as Urushibara nickel, metallic catalysts prepared by reducing nickel oxide or mixtures of nickel oxide and at least one other metal oxide with hydrogen, nickel oxide or mixtures of nickel oxide and at least one other metal oxide, such as nickel oxide/chromium oxide, nickel oxide/manganese oxide/copper oxide or nickel oxide/chromium oxide/copper oxide, or supported catalysts, such as nickel-on-kieselguhr, nickel-on-aluminium oxide, nickel/copper-on-aluminium oxide or nickel/manganese on-alumininium oxide.

Particularly preferred catalysts are Raney nickel, Raney nickel/iron, Raney nickel/cobalt, Raney nickel/copper, nickel-on-aluminium oxide, nickel-on-kieselguhr, nickel and nickel oxide/chromium oxide.

The catalysts mentioned can be used individually or as mixtures of 2 or more of these catalysts. The amount in which the catalyst or catalyst mixture is used can vary within wide limits. In a discontinuous procedure, the amount can be, for example, from 1 to 100% by weight, preferably from 5 to 50% by weight, of catalyst metal, relative to the amount of neopentanol employed. For the continuous procedure, the amount of catalyst can be, for example, from 5 to 500% by weight, preferably 5 to 250% by weight, of catalyst metal, relative to the amount of neopentanol employed per hour. If the process according to the invention is carried out by a discontinuous procedure, the hydrogenation catalysts mentioned can be repeatedly employed. In the case of a continuous procedure, they have outstandingly long service lives. It is thus also in all cases economical to use high catalyst concentrations within the ranges indicated.

In principle, hydrogen can optionally be simultaneously used in carrying out the process according to the invention. The procedure in the presence of hydrogen is the preferred variant of the process, since particularly high service lives for the catalysts and a particularly high selectivity with respect to the reaction of neopentanol to form neopentylamine are thereby achieved. The use of a large excess of hydrogen, relative to the neopentanol employed, does no harm to the process according to the invention. However, a large excess of hydrogen is inappropriate for an industrial process. It is thus particularly favourable that the process according to the invention already exhibits the described advantages of high catalyst service life and high selectivity in the presence of catalytic amounts of hydrogen. A catalytic amount of hydrogen is, for example, 0,001 to 1 mol, preferably 0.001 to 0.5 mol, relative to the neopentanol employed. An amount of hydrogen between 0.01 and 0.1 mol per mol of neopentanol is particularly preferred.

The hydrogen optionally used for carrying out the process according to the invention can be employed as molecular hydrogen or can be hydrogen which has been split off from a suitable substance under the conditions of the process according to the invention. Examples of substances suitable for this are tetralin, decalin, cyclohexane and isobutane. Molecular hydrogen is preferably employed.

The reaction of the process according to the invention can be illustrated by the following equation:

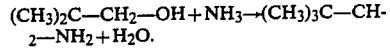

$$(CH_3)_2C-CH_2-OH + NH_3 \rightarrow (CH_3)_3C-CH_2-NH_2 + H_2O.$$

The process according to the invention can be carried out, for example, as follows:

For a discontinuous procedure in the liquid phase, the neopentanol, the hydrogenation catalyst and liquid ammonia are introduced into a stirred autoclave. Hydrogen is subsequently forced in until the desired pressure is reached. The mixture is then heated to the chosen reaction temperature for some hours, whilst stirring. After cooling and letting down, the catalyst is separated off from the reaction mixture, for example by filtration, and the filtrate thus obtained is worked up by suitable methods, such as distillation, extraction or crystallization, to give pure neopentylamine.

For carrying out the process according to the invention continuously in the liquid phase, a mixture of neopentanol and liquid ammonia is pumped over the hydrogenation catalyst in a pressure tube under the chosen pressure and at the chosen reaction temperature, catalytic amounts of hydrogen optionally being simultaneously fed in. After leaving the pressure tube the reaction mixture can be worked up in the same manner as described above. A procedure can also be followed in which, in a manner which is in itself known, a mixture of neopentanol and liquid ammonia is passed in circulation over the hydrogenation catalyst in the pressure tube, catalytic amounts of hydrogen optionally being fed in, and downstream of the hydrogenation catalyst only some of the circulating stream is removed and worked up, whilst appropriate amounts of neopentanol and liquid ammonia, and optionally catalytic amounts of hydrogen, are continuously fed to the circulating stream upstream of the hydrogenation catalyst. It is not critical to the success of the process according to the invention for a certain pressure to be maintained, as long as it is ensured that the total pressure of the system is considerably greater than the vapour pressure of the reaction mixture at the chosen reaction temperature.

In all the variants described for the process according to the invention, the ammonia which has not been consumed and the unreacted neopentanol can be recovered during working up of the reaction mixture and recycled again into the process according to the invention.

The neopentylamine which can be prepared in the process according to the invention is virtually free from amines with a higher degree of alkylation and thus in many cases does not need to be subjected to an additional separation operation. A neopentylamine which is virtually free from amines with a higher degree of alkylation is a neopentylamine with a content of amines with a higher degree of alkylation of at most 3% by weight, preferably at most 1% by weight, relative to the amount of neopentylamine.

It is surprising that mono-neopentylamine is obtained with high selectivity from neopentanol with a relatively small excess of ammonia in the process according to the invention.

The neopentylamine which can be prepared by the process according to the invention is an important intermediate product for the preparation of herbicidally active 1-neopentyl-tetrahydro-1,3,5-triazine-2,6-diones according to DE-OS (German Published Specification) No. 2,254,200, in which, for example, neopentylamine is reacted with a 1-alkyl-tetrahydro-1,3,5-triazine-2,6-dione, or neopentylamine is first converted into N-neopentyl-bis-(chlorocarbonyl)-amine by phosgenation and this compound is reacted with a substituted formamide or hydrochloride thereof.

EXAMPLE 1

1.5 $l_{25°\ C.}$ (53 mols) of liquid ammonia, 1.5 $l_{65°\ C.}$ (13.4 mols) of neopentanol and 6.7 $l_{25°\ C.}$ (0.3 mol) of gaseous hydrogen per hour are pumped, under 200 bars, through a reaction tube which is 50 mm in diameter and 340 mm in length and is filled with 1.3 kg of Raney nickel pills. The temperature in the pressure tube is 230° C. The reaction mixture is let down to 16 bars and ammonia is distilled off in a pressure column. 1,183 kg per hour of a mixture consisting of water to the extent of 5%, neopentylamine to the extent of 22.9% and neopentanol to the extent of 70.3% is obtained at the bottom of the column. The yield of neopentylamine is 24% and the selectivity is 87.7% of theory.

EXAMPLES 2 TO 5

These examples are carried out analogously to Example 1. The numerical data are summarized in Table 1. After being in use for 14 days, the catalyst shows no loss in activity.

EXAMPLE 6

0.75 $l_{25°\ C.}$ (26.5 mols) of liquid ammonia, 1.5 $l_{65°\ C.}$ (13 mols) of neopentanol and 6.7 $l_{25°\ C.}$ (0.3 mol) of gaseous hydrogen per hour are pumped, under 250 bars, through a reaction tube which is 50 mm in diameter and 340 mm in length and with 0.56 kg of nickel-on-kieselguhr tablets (nickel content: 52%). The temperature in the pressure tube is 250° C. After distilling off the ammonia, 1,210 kg per hour of a mixture consisting of water to the extent of 15%, neopentylamine to the extent of 71.3% and neopentanol to the extent of 12.8% are obtained at the bottom of the column. The yield of neopentylamine is 76.3% and the selectivity is 88.2% of theory.

down and carefully emptied. The reaction mixture, from which the catalyst has been separated off by filtration, contains, in addition to 86 g of neopentylamine (yield: 83% of theory) also 10.5 g of starting material (conversion: 90%) and 8 g of by-products, mainly pivalic acid amide. This corresponds to a selectivity of 92%. Pure neopentylamine is isolated from the mixture by fractional distillation.

EXAMPLES 8 TO 10

If the catalysts listed in Table 2 are used instead of the Raney nickel/iron catalyst in the procedure described in Example 7, the results given in the same table are obtained.

TABLE 2

| Example | Catalyst | Conversion % | Yield % of theory | Selectivity % |
|---|---|---|---|---|
| 8 | Raney nickel | 82 | 72 | 88 |
| 9 | Raney cobalt | 55 | 49 | 89 |
| 10 | Nickel chromite (53% of Ni, 18% of $Cr_2O_3$) | 53 | 46 | 86.5 |

What is claimed is:

1. A process for the preparation of neopentylamino which is virtually free from amines with a higher degree of alkylation which comprises contacting neopentanol with ammonia at a temperature of 200° to 300° C. in the presence of a hydrogenation catalyst.

2. A process according to claim 1, wherein the reaction is carried out in the liquid phase under a pressure of at least 10 bars.

3. A process according to claim 1, wherein the reaction is carried out continuously.

4. A process according to claim 1, wherein 0.5 to 10 mols of ammonia are employed per mol of neopentanol.

5. A process according to claim 1, wherein 1 to 5 mols of ammonia are employed per mol of neopentanol.

6. A process according to claim 1, wherein the reaction is carried out in the presence of 0.001 to 1 mol of hydrogen per mol of neopentanol.

7. A process according to claim 1, wherein the hydrogenation catalyst contains at least one metal from group VIII of the periodic system (Mendeleev) and/or copper

TABLE 1

| Example | NH$_3$ $l_{25°\ C.}$ hours$^{-1}$ | mols hours$^{-1}$ | Neopentanol $l_{65°\ C.}$ hours$^{-1}$ | mols hours$^{-1}$ | H$_2$ $l_{25°\ C.}$ hours$^{-1}$ | Reaction temperature °C. | Reaction mixture kg hours$^{-1}$ | Content % of neopentylamine | % of neopentanol | Yield % of neopentylamine | Selectivity % of theory |
|---|---|---|---|---|---|---|---|---|---|---|---|
| 2 | 0.55 | 19.4 | 0.94 | 8.1 | 6.7 | 230 | 0.794 | 44.7 | 41.1 | 50.3 | 92.7 |
| 3 | 0.75 | 26.5 | 0.75 | 6.5 | 6.7 | 230 | 0.640 | 46.8 | 39.9 | 53.0 | 95.7 |
| 4 | 0.38 | 13.4 | 0.38 | 3.3 | 6.7 | 230 | 0.330 | 56.5 | 26.5 | 64.9 | 92.9 |
| 5 | 1.5 | 53 | 1.5 | 13 | 6.7 | 240 | 1.195 | 38.4 | 55.2 | 40.6 | 95.8 |

EXAMPLE 7

A 0.7 l stirred autoclave is charged with 115 g of neopentyl alcohol (water content: 9% by weight) and 45 g of Raney nickel/iron (iron content: 15% by weight) and 45 g of Raney nickel/iron (iron content: 15% by weight) and is flushed with nitrogen and hydrogen until free from air. 180 ml of liquid ammonia are then added at room temperature and hydrogen is forced in until the pressure reaches 30 bars. The mixture is subsequently heated to 265° C., whilst stirring, and the reaction is carried out at this temperature for 6 hours, during which a pressure of about 300 bars is established. After cooling to room temperature, the autoclave is let or at least one of these metals in combination with at least one metal from the group comprising vanadium, chromium and manganese, in metallic and/or oxidic form.

8. A process according to claim 1, wherein the catalyst contains nickel in metallic or oxidic form.

9. A process according to claim 1, wherein the process is carried out in the presence of hydrogen.

10. A process according to claim 9, wherein 0.5 to 10 mols of ammonia are employed per mol of neopentanol.

11. A process according to claim 10, wherein 1 to 5 mols of ammonia are employed per mol of neopentanol.

* * * * *

UNITED STATES PATENT AND TRADEMARK OFFICE
CERTIFICATE OF CORRECTION

PATENT NO. : 4,495,369

DATED : January 22, 1985

INVENTOR(S) : Friedrich Werner et al

It is certified that error appears in the above-identified patent and that said Letters Patent is hereby corrected as shown below:

On the title page;

after "[75] Inventors:"     2nd line, delete "Gramm" and substitute --Cramm--

Col. 1, line 62     Delete "these" and substitute --those--

Col. 4, line 6     Delete "$(CH_3)_2$" and substitute --$(CH_3)_3$--

Signed and Sealed this

Twenty-third Day of July 1985

[SEAL]

Attest:

DONALD J. QUIGG

*Attesting Officer*     *Acting Commissioner of Patents and Trademarks*